(12) United States Patent
Hosoya et al.

(10) Patent No.: US 8,748,093 B2
(45) Date of Patent: Jun. 10, 2014

(54) **METHOD OF DETECTING FUNGI BELONG TO GENUS *GEOSMITHIA***

(75) Inventors: Kouichi Hosoya, Tochigi (JP); Motokazu Nakayama, Tochigi (JP); Hajime Tokuda, Tochigi (JP); Takashi Yaguchi, Chiba (JP); Yusuke Hiro, Chiba (JP)

(73) Assignee: Kao Corporation, Tokyo (JP)

( * ) Notice: Subject to any disclaimer, the term of this patent is extended or adjusted under 35 U.S.C. 154(b) by 331 days.

(21) Appl. No.: 13/128,114

(22) PCT Filed: Nov. 11, 2009

(86) PCT No.: PCT/JP2009/069225
§ 371 (c)(1),
(2), (4) Date: Jul. 19, 2011

(87) PCT Pub. No.: WO2010/055868
PCT Pub. Date: May 20, 2010

(65) Prior Publication Data
US 2012/0129166 A1    May 24, 2012

(30) Foreign Application Priority Data
Nov. 11, 2008    (JP) .................................. 2008-288639

(51) Int. Cl.
*C12Q 1/68*    (2006.01)

(52) U.S. Cl.
CPC .................................. *C12Q 1/6895* (2013.01)
USPC ......... 435/6.1; 435/6.11; 435/6.12; 435/6.15; 435/91.1; 435/91.2; 536/23.1; 536/24.3; 536/24.32

(58) Field of Classification Search
None
See application file for complete search history.

(56) References Cited

U.S. PATENT DOCUMENTS 6,117,636 A    9/2000    Chrzavzez née Taddei et al.

FOREIGN PATENT DOCUMENTS

| JP | 2006-061152 A | 3/2006 | | |
|----|---------------|--------|---|---|
| JP | 2006-304763 A | 11/2006 | | |
| JP | 2007-174903 A | 7/2007 | | |
| WO | WO2009145279 | * 12/2009 | ............... | C12Q 1/68 |
| WO | WO2009145314 | * 12/2009 | ............... | C12Q 1/68 |

OTHER PUBLICATIONS

International Search Report (ISR) for PCT/JP2009/069225, I.A. fd: Nov. 11, 2009, mailed Dec. 8, 2009 from the Japanese Patent Office, Tokyo, Japan.
International Preliminary Report on Patentability (IPRP), Chapter I of the Patent Cooperation Treaty, including the Written Opinion for PCT/JP2009/069225, I.A. fd: Nov. 11, 2009, issued Jun. 21, 2011 from the International Bureau of WIPO, Geneva, Switzerland.
Luangsa-ard, J.J., Definition: *Talaromyces emersonii* beta-tubulin-like gene, partial sequence, Database DDBJ/EMBL/GenBank [online], Accession No. AY766255, Dec. 30, 2005 uploaded, [retieval date Nov. 26, 2009], <http://www.ncbi.nlm.nih.gov/sviewer/viewer.fcgi?62178535:NCBI:12414018>.
Peterson, S.W., Definition: *Talaromyces emersonii* strain NRRL 3221 beta-tubulin gene, partial cds, Database DDBJ/EMBL/GenBank [online], Accession No. EU021666, Jun. 11, 2008 uploaded, [retrieval date Nov. 26, 2009], <http://www.ncbi.nlm.nih.gov/sviewer/viewer.fcgi?158139038:NCBI:23028565>.
Luangsa-ard, J.J., Definition: *Talaromyces byssochlamydoides* strain CBS 413.71 beta-tubulin gene, partial sequence, Database DDBJ/EMBL/GenBank [online], Accession No. AY753374, Mar. 30, 2006 uploaded, [retrieval date Nov. 26, 2009], <http://www.ncbi.nlm.nih.gov/sviewer/viewer.fcgi?62999472:NCBI:13130226>.
Aoyama, F., "Identification of heat resistance fungi in fruit juice based on DNA sequence analysis" ("Kajitsu Inryochu ni Okeru Tainetsusei Kabi no DNA Dotei"), Kaju Kyokaiho No. 569, pp. 4-15 (2006).
Yaguchi, T. "Fungal experiment technology lecture 1: Collection / the detection and the separation of fungi: The separation method of soil straight *Aspergillus*, *Penicillium* and the teleomorph" ("Kinrui no Saishu•Kenshutsu to Bunri:Dojosei *Aspergillus*, *Penicillium* Oyobi sono Teleomorph no Bunriho"), Transactions of the Mycological Society of Japan 38(2):101-104 (1997), Mycological Society of Japan, Tokyo, Japan.
Yaguchi, T. et al., "Two new species of *Talaromyces* from Taiwan and Japan," Mycoscience 35:249-255 (1994), Mycological Society of Japan, Tokyo, Japan.
Collings, A et al., "Endo-β-1,4-glucanase, exo-β-1,4-glucanase, β-glucosidase and related enzyme activity in culture filtrates of thermophilic, thermotolerant and mesophilic filamentous fungi," Microbio 56:131-147 (1988), The Faculty Press, Cambridge, Great Britain.
Udagawa, Shun'ichi, "A problem of the foodstuffs mycology—harm by the heat-resistant mold" (Shokuhin Kingaku no Kadai-Tainetsusei Kabi ni yoru Kigai), Mycotoxins 50:3-11 (2000), Japanese Society of Mycotoxicology, Japan.
Inoue, J. et al., "The selection of the primer in the PCR" ("PCR ni Okeru Primer no Sentaku"), Chapter 2 in The State of the Art of the PCR Method (Jikken Igaku Bessatsu Bio Manual Up Series PCT-ho no Saishin Gijutsu), 4th print, Hayashi, K., ed, pp. 18-19, 1998, Yodosha Co., Ltd., Japan.

(Continued)

*Primary Examiner* — Jeanine A Goldberg
(74) *Attorney, Agent, or Firm* — Sterne, Kessler, Goldstein & Fox P.L.L.C.

(57) ABSTRACT

A method of detecting a fungus belonging to genus *Geosmithia*, including identifying a fungus belonging to genus *Geosmithia* using a nucleic acid represented by the nucleotide sequence defined in the following (a) or (b):
(a) a partial nucleotide sequence of β-tubulin gene shown in any one of SEQ ID NOS: 1 to 3, or a complementary sequence thereof;
(b) a nucleotide sequence including deletion, substitution, insertion or addition of one or several nucleotide(s) in the nucleotide sequence shown in any one of SEQ ID NOS: 1 to 3, or a complementary sequence thereof.

10 Claims, 1 Drawing Sheet

(56) References Cited

OTHER PUBLICATIONS

Hosoya, K et al., "Identification method of identification of the master of foodstuffs harm bacteria thermostability mould 4 strains required, 1. Establishment of the polymerase chain reaction" (Shokuhin Kigaikin Tainetsusei Kabi Shuyo 4-kinshu no Shikibetsu Doteiho 1. PCR-ho no Kakuritsu), The 29th Nippon Shokuhin microorganism institute science general meeting, a collection of lecture syllabus, Japanese Society of Food Microbiology Gakujutsu Sokai Koen Yoshishu, Nov. 12, 2008, p. 55, MEDDCO Co., Ltd., Japan.

Extended European Search Report pursuant to Rule 62 EPC for EP Appl. No. 09826115.9, including the supplementary European search report and the European search opinion, mailed May 22, 2012, European Patent Office, Munich, Germany.

Unverified human translation of a report by Aoyama, F., "Identification of heat resistance fungi in fruit juice based on DNA sequence analysis," Kajitsu Kyohaiho, Association of Fruit Juice, Report No. 569, pp. 4-15, Japan Fruit Juice Association, Tokyo, Japan (Jan. 2006).

Aoyama, F., *Penicillium genus* beta tubulin polynucleotide SEQ ID No. 258, Database Geneseq [online], Accession No. AEM20041, Jan. 25, 2007 uploaded.

Boutros, M., et al., Fruit fly asfl gene amplifying PCR primer 1A, Database Geneseq [online], Accession No. AEM72406, Mar. 8, 2007 uploaded.

Houbraken, J., et al., "Sexual reproduction as the cause of heat resistance in the food spoilage fungus *Byssochlamys spectabilis* (Anamorph *Paecilomyces variotii,*)" *Applied and Environmental Microbiology* 74: 1613-1619 (Mar. 2008), American Society for Microbiology, United States.

Peterson, S.W., "Phylogenetic analysis of *Aspergillus* species using DNA sequences from four loci," *Mycologia* 100:205-226 (Mar. 2008), The Mycological Society of America, United States.

Pryce-Miller, E., et al., "Enviromental detection of *Penicillium marneffei* and growth in soil mircocosms in competion with *Talaromyces stipitatus,*" *Fungal Ecology* 1:49-56 (Apr. 2008), Elsevier Ltd. and The British Mycologiocal Society, United Kingdom.

\* cited by examiner

SEQUENCE LISTING

```
<160> NUMBER OF SEQ ID NOS: 7

<210> SEQ ID NO 1
<211> LENGTH: 505
<212> TYPE: DNA
<213> ORGANISM: Geosmithia eburneus

<400> SEQUENCE: 1
ggtaaccaaa tcggtgctgc tttctggtag gtcaacactt accaccaaca agagagctcg      60
agtcgccctc acattcgagc ttagtggaca ttgtactctc taggatgagc atgctgacca     120
tttcccaggc aaaccatatc aggcgagcat ggccttgatg gctccggagt gtgagtgtca     180
atgcttgatt tgggagaagg aggactctcg tcctgactga tcttggcaca tagctacaat     240
ggctcctccg acctccagct cgagcgtatg aacgtctact ttaatgaggt tggtagatct     300
aatgggtaat cgacgtgcca tgcgctgatc ggtggaacag gccagcggta acaagtatgt     360
gcctcgtgcc gtcctcgtcg acctggaacc cggcagccat ggacgccgta ccgtgccggt     420
cctttcggcc agctttccg ccccgacaac ttcgtcttcg gtcagtctgg tgccggtaac     480
aactgggcca agggtcacta cactg                                           505

<210> SEQ ID NO 2
<211> LENGTH: 474
<212> TYPE: DNA
<213> ORGANISM: Geosmithia byssochlamydoides

<400> SEQUENCE: 2
ggtaaccaaa tcggtgctgc tttctggtag gtcgacaaca gagctcgcgt cgccctcgcg      60
ttcgagctca atggacatca tatagaatta gcgtgctgac tgtttcccag gcaaaccatc     120
tctggcgagc atggccttga cggctccgga gtgtgagtgt tgaatttcaa aggaaaagaa     180
cgttggtcct gactattggc acagctacaa tggctcctct gacctccagc tggagcgtat     240
gaacgtctac ttcaacgagg ttagtggatc tgacaggaaa tcgacgagtc acacgctgat     300
cggtcaacca ggccagcggt aacaagtatg tgcctcgtgc cgtcctggtc gacctggagc     360
```

```
ccggtaccat ggacgccgtc cgtgccggtc ctttcggcca gcttttccgc cccgacaact    420
tcgtcttcgg tcagtccggt gctggtaaca actgggccaa gggtcactac actg          474

<210> SEQ ID NO 3
<211> LENGTH: 461
<212> TYPE: DNA
<213> ORGANISM: Geosmithia emersonii

<400> SEQUENCE: 3
ggtaaccaaa tcggtgctgc tttctggtaa gtcgacaagc tcgtgtggcc tcgcgttcga     60
gttgaatagg acgctgacct tttcccaggc aaaccatctc tggcgagcat ggccttgacg    120
gctccggagt gtgagtgttg ttcgtgattt cgggagaaaa ggactcccat cctgactgat    180
tttggcacag ctacaatggc tcctctgacc ttcagctgga gcgtatgaac gtctacttca    240
acgaggttgg tgagacctgt ctgacgaacg atctaaatca ctgaaccatg aagcaggcca    300
gcggtaacaa gtatgtgcct cgtgccgtcc tgtgtgcgac ctggagcccg ataccatgga    360
cgccgtccgt gccggtcctt tcaaacagct tttccgcccc gacaacttca tcttcggtca    420
gtccagtgct ggtaacaact ggaccaaggg tcactacact g                        461

<210> SEQ ID NO 4
<211> LENGTH: 18
<212> TYPE: DNA
<213> ORGANISM: Artificial sequence
<220> FEATURE:
<223> OTHER INFORMATION: Oligonucleotide designed from the nucleotide
      sequence of Geosmithia

<400> SEQUENCE: 4
gtggccctca cgttcgag                                                   18

<210> SEQ ID NO 5
<211> LENGTH: 20
<212> TYPE: DNA
<213> ORGANISM: Artificial sequence
<220> FEATURE:
<223> OTHER INFORMATION: Oligonucleotide designed from the nucleotide
      sequence of Geosmithia

<400> SEQUENCE: 5
gccattgtag catgtgccaa                                                 20

<210> SEQ ID NO 6
<211> LENGTH: 24
<212> TYPE: DNA
<213> ORGANISM: Artificial sequence
<220> FEATURE:
<223> OTHER INFORMATION: Oligonucleotide for sequencing the nucleotide
      sequence of Geosmithia, primer Bt2a

<400> SEQUENCE: 6
ggtaaccaaa tcggtgctgc tttc                                            24

<210> SEQ ID NO 7
<211> LENGTH: 24
<212> TYPE: DNA
<213> ORGANISM: Artificial sequence
<220> FEATURE:
<223> OTHER INFORMATION: Oligonucleotide for sequencing the nucleotide
      sequence of Geosmithia, primer Bt2b
```

```
<400> SEQUENCE: 7
accctcagtg tagtgaccct tggc                                          24
```

METHOD OF DETECTING FUNGI BELONG TO GENUS *GEOSMITHIA*

REFERENCE TO SEQUENCE LISTING SUBMITTED ELECTRONICALLY

The content of the electronically submitted substitute sequence listing, file name 2537_0510000SEQIDListing.txt, size 3,592 bytes; and date of creation Jul. 24, 2013, filed herewith, is incorporated herein by reference in its entirety.

TECHNICAL FIELD

The present invention relates to a method of detecting fungi belonging to genus *Geosmithia*.

BACKGROUND ART

Fungi belonging to genus *Geosmithia* are widely found throughout nature, and the fungi grow proliferously in agricultural crops such as vegetables and fruits to thereby contaminate foods and drinks made from the agricultural crops. Since fungi belonging to genus *Geosmithia* form chlamydospores having high heat resistance, the fungi may survive, proliferate, and cause mold growth even after usual sterilization effective against other fungi, such as heat sterilization for acidic drinks. Therefore, there are concerns about the fungi belonging to genus *Geosmithia* as important harmful fungi causing severe quality accidents. To prevent the accidents by the fungi belonging to genus *Geosmithia* in foods and drinks and raw materials thereof, it is particularly important to detect and identify the fungi belonging to genus *Geosmithia*.

At present, fungi belonging to genus *Geosmithia* are detected and identified by observing the morphological features of the cultured fungi. In this method, it is necessary to continue the culture until morphological characters appear, and hence, it takes a long period of time (at least 14 days) to achieve the method. Further, the identification of the fungi based on microscopic morphological features requires a high level expertise, and it can not be denied that the identification results may vary depending on judges. Also in some cases, fungi damaged by heating, a chemical agent or the like lose morphogenetic ability, and such fungi cannot form characteristic morphology even after long-term cultivation, thus, the result of the identification is less reliable. Such detection of fungi requiring a long time is not always satisfactory in view of food and drink sanitation, keeping of raw material freshness, distributional restrictions, and the like. Therefore, it is required to establish a detection and identification method which solves the problems of rapidness and reliability.

As a rapid and reliable method of detecting fungi, an amplification method which targets a specific nucleotide sequence of a gene (such as the PCR method) is known (see, for example, Patent Literatures 1 to 4). However, a gene region specific to fungi belonging to genus *Geosmithia* has not been clarified. Therefore, such method has a problem in that it is difficult to detect fungi belonging to genus *Geosmithia* specifically and rapidly.

PRIOR ART LITERATURE

Patent Literatures

Patent Literature 1: JP-T-11-505728 ("JP-T" means searched and published International patent publication)

Patent Literature 2: JP-A-2006-61152 ("JP-A" means unexamined published Japanese patent application)
Patent Literature 3: JP-A-2006-304763
Patent Literature 4: JP-A-2007-174903

SUMMARY OF INVENTION

The present invention is contemplated for providing a method capable of specifically, simply and quickly detecting fungi belonging to genus *Geosmithia*, which is one of microorganisms mainly responsible for contamination of foods and drinks. Further the present invention is contemplated for providing a DNA represented by a nucleotide sequence specific to fungi belonging to genus *Geosmithia*, an oligonucleotide capable of hybridizing with a nucleic acid represented by the nucleotide sequence, and a primer pair and a detection kit containing the oligonucleotide, which are for use in the above detection method.

In view of such problems, the inventors of the present invention have made extensive studies to provide a method of specifically discriminating fungi belonging to genus *Geosmithia*. As a result, the inventors have found out that the β-tubulin gene of fungi belonging to genus *Geosmithia* includes a region having a specific nucleotide sequence which can be clearly distinct from that of another fungi (hereinafter, also referred to as "variable region"). Moreover, the inventors have found out that such fungi belonging to genus *Geosmithia* can be detected specifically and rapidly by targeting the variable region. The present invention has been completed based on these findings.

The present invention resides in a method of detecting a fungus belonging to genus *Geosmithia*, including identifying a fungus belonging to genus *Geosmithia* using a nucleic acid represented by the nucleotide sequence defined in the following (a) or (b):

(a) a partial nucleotide sequence of β-tubulin gene shown in any one of SEQ ID NOS: 1 to 3, or a complementary sequence thereof;

(b) a nucleotide sequence including deletion, substitution, insertion or addition of one or several nucleotide(s) in the nucleotide sequence shown in any one of SEQ ID NOS: 1 to 3, or a complementary sequence thereof.

Further, the present invention resides in a DNA represented by the nucleotide sequence defined in the above (a) or (b), which is used for detecting a fungus belonging to genus *Geosmithia*.

Further, the present invention resides in an oligonucleotide for detecting a fungus belonging to genus *Geosmithia*, which is hybridizable with a nucleic acid represented by the nucleotide sequence defined in the above (a) or (b) and can act as a nucleic acid probe or nucleic acid primer for specifically detecting a fungus belonging to genus *Geosmithia*.

Further, the present invention resides in the oligonucleotide for detecting a fungus belonging to genus *Geosmithia*, wherein the above-described oligonucleotide for detection is the oligonucleotide defined in the following (c) or (d), and a kit for detecting a fungus belonging to genus *Geosmithia*, containing the oligonucleotide defined in the following (c) or (d):

(c) an oligonucleotide represented by the nucleotide sequence shown in SEQ ID NO: 4 or the complementary sequence thereof, or an oligonucleotide which is represented by a nucleotide sequence sharing 70% or more identity with the nucleotide sequence shown in SEQ ID NO: 4 or the complementary sequence thereof and can be used as an oligonucleotide for detection;

(d) an oligonucleotide represented by the nucleotide sequence shown in SEQ ID NO: 5 or the complementary sequence, thereof, or an oligonucleotide which is represented by a nucleotide sequence sharing 70% or more identity with the nucleotide sequence shown in SEQ ID NO: 5 or the complementary sequence thereof and can be used as an oligonucleotide for detection.

Further, the present invention resides in a nucleic acid primer pair for detecting a fungus belonging to genus *Geosmithia*, containing the oligonucleotides defined in the following (e) and (f); and a kit for detecting a fungus belonging to genus *Geosmithia* containing this primer pair:

(e) an oligonucleotide represented by the nucleotide sequence shown in SEQ ID NO: 4, or an oligonucleotide represented by a nucleotide sequence which shares 70% or more identity with the nucleotide sequence shown in SEQ ID NO: 4 and can be used as a nucleic acid primer;

(f) an oligonucleotide represented by the nucleotide sequence shown in SEQ ID NO: 5, or an oligonucleotide represented by a nucleotide sequence which shares 70% or more identity with the nucleotide sequence shown in SEQ ID NO: 5 and can be used as a nucleic acid primer.

According to the present invention, a method capable of specifically, simply and quickly detecting fungi belonging to genus *Geosmithia*, which is one of microorganisms mainly responsible for contamination of foods and drinks, can be provided. Further, according to present invention, a DNA represented by a nucleotide sequence specific to fungi belonging to genus *Geosmithia* for use in the detection method, an oligonucleotide capable of hybridizing with a nucleic acid represented by the nucleotide sequence, and a primer pair and a detection kit containing the oligonucleotide can be provided.

Other and further features and advantages of the invention will appear more fully from the following description, appropriately referring to the accompanying drawings.

DESCRIPTION OF EMBODIMENTS

Figure 1:
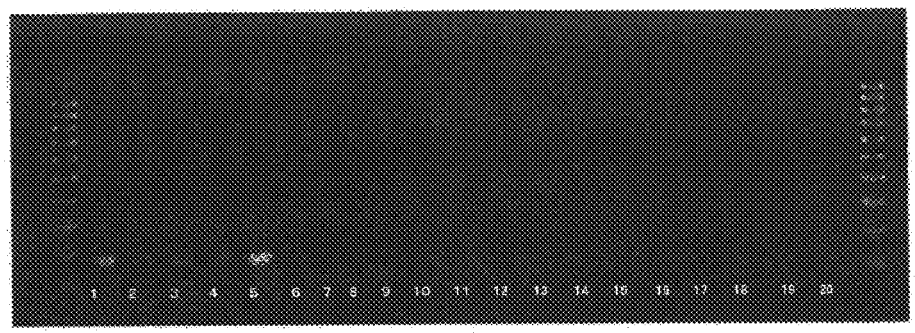
FIG. 1 An electrophoretogram of PCR products in Examples.

Hereinafter, the present invention is described in detail.

The present invention is a method of specifically discriminating and detecting fungi belonging to genus *Geosmithia* by identifying the fungi belonging to genus *Geosmithia* using a nucleic acid represented by a specific partial nucleotide sequence of the β-tubulin gene of the fungi belonging to genus *Geosmithia*, i.e., a nucleic acid represented by a nucleotide sequence in a region (variable region) which is present in the β-tubulin gene sequence of the fungi belonging to genus *Geosmithia* and is specific to genus *Geosmithia*.

In the present invention, "fungi belonging to genus *Geosmithia*" are one of filamentous Deuteromycetes. In the life cycle of asexual generation, fungi belonging to genus *Geosmithia* form chlamydospores having high heat resistance, which can survive even after heating at 70° C. for 30 minutes. Among fungi belonging to genus *Geosmithia*, particularly harmful species include *Geosmithia eburneus*, *Geosmithia byssochlamydoides*, and *Geosmithia emersonii*. In the present invention, fungi belonging to genus *Geosmithia* also include *Talaromyces* (*Rasamsonia*) *eburneus*, *Talaromyces* (*Rasamsonia*) *byssochlamydoides*, and *Talaromyces* (*Rasamsonia*). *emersonii*, which are the sexual generation of the genus.

The "β-tubulin" is a protein which constitutes a microtubule, and the "β-tubulin gene" is a gene encoding β-tubulin. In the present invention, the "variable region of the β-tubulin gene" is a particular region where nucleotide mutations tend to accumulate in the β-tubulin gene. In the detection method of the present invention, "identifying . . . using a nucleic acid represented by a partial nucleotide sequence of the β-tubulin gene" means that the identification is performed using a nucleic acid represented by the whole or a part of the partial nucleotide sequence.

The detection method of the present invention is characterized by using a nucleic acid represented by a nucleotide sequence in a specific (variable) region of the β-tubulin gene of fungi belonging to genus *Geosmithia*.

The inventors have determined the nucleotide sequences of the β-tubulin genes of various fungi including fungi belonging to genus *Geosmithia* and analyzed the genetic distance and nucleotide sequence identity between fungi genera. Specifically, the inventors have determined the nucleotide sequence of the β-tubulin gene of each fungi by sequencing method and made a study on common nucleotide regions by alignment analysis. As a result, the inventors have found that the β-tubulin genes have a certain region (variable region) that is highly conservative among the same genus but less conservative among different genera, namely, having a genus-specific nucleotide sequence. Fungi belonging to genus *Geosmichia* have a specific nucleotide sequence in this variable region. Therefore, the region is useful as a genetic index for discrimination and identification of fungi belonging to genus *Geosmithia* at a genus-level.

The inventors have further made a study on partial regions, which are selected from the variable region and satisfy the following four conditions: 1) including a region containing about 10 continuous nucleotides which are derived from the gene and have a nucleotide sequence specific to fungi belonging to genus *Geosmithia*; 2) GC content of the oligonucleotide is about 30% to 80%; 3) possibility to cause self-annealing in the oligonucleotide is low; and 4) Tm value (melting temperature) of the oligonucleotide is about 55° C. or more. As a result, the inventors have found 15 to 25 base oligonucleotides derived from the nucleotide sequence of the variable region.

In the present invention, such variable regions and oligonucleotides derived from such variable regions are used as targets.

The nucleic acid represented by the partial nucleotide sequence of the β-tubulin gene of fungi belonging to genus *Geosmithia* to be used in the detection method of the present invention (the nucleotide sequence in the variable region) is a nucleic acid represented by the nucleotide sequence shown in SEQ ID NO: 1, 2 or 3 or the complementary sequence thereof.

The nucleotide sequence shown in SEQ ID NO: 1 and the complementary sequence thereof are nucleotide sequences of the variable region of the β-tubulin gene, which is isolated and identified from *Geosmithia eburneus*. The nucleotide sequence shown in SEQ ID NO: 2 and the complementary sequence thereof are nucleotide sequences of the variable region of the β-tubulin gene, which is isolated and identified from *Geosmithia byssochlamydoides*. The nucleotide sequence shown in SEQ ID NO: 3 and the complementary sequence thereof are nucleotide sequences of the variable region of the β-tubulin gene, which is isolated and identified from *Geosmithia emersonii*. These sequences have very high identity among fungi belonging to genus *Geosmithia* and have low identity to fungi other than fungi belonging to genus *Geosmithia*, and hence, it is possible to specifically distinguish and identify only fungi belonging to genus *Geosmithia* by confirming whether a test sample has such nucleotide sequence or not.

Also in the case of using nucleic acids represented by the nucleotide sequence including deletion, substitution, insertion or addition of one or several nucleotide(s) in the nucleotide sequence shown in SEQ ID NO: 1, 2 or 3, or complementary sequence thereof, it is possible to specifically distinguish and identify only fungi belonging to genus *Geosmithia*. As used herein, the term "one or several" preferably means 1 to 25, more preferably 1 to 20, even more preferably 1 to 15, still more preferably 1 to 10, further more preferably 1 to 5.

(Hereinafter, the nucleotide sequence shown in SEQ ID NO: 1, 2 or 3, or the complementary sequence thereof, and the nucleotide sequence including deletion, substitution, insertion or addition of one or several nucleotide(s) in the nucleotide sequence shown in SEQ ID NO: 1, 2 or 3, or the complementary sequence thereof are, as a whole, also referred to as "nucleotide sequence in variable region of the β-tubulin gene of the present invention".)

The method of identifying fungi belonging to genus *Geosmithia* using a nucleic acid represented by the nucleotide sequence in the variable region of the β-tubulin gene of the present invention is not particularly limited, and may be performed by a usual genetic engineering procedure such as a sequencing method, a hybridization method, a PCR method, or a LAMP method.

In the detection method of the present invention, in order to identify fungi belonging to genus *Geosmithia* using the nucleic acid represented by the nucleotide sequence in the variable region of the β-tubulin gene of the present invention, the nucleotide sequence of the β-tubulin gene in a sample is preferably determined to confirm whether the nucleotide sequence of the gene includes the nucleotide sequence of the nucleic acid defined in the above (a) or (b), or not. That is, the detection method of the present invention includes: analyzing and determining the nucleotide sequence of the β-tubulin gene in a sample; comparing the determined nucleotide sequence with the nucleotide sequence in the variable region of the β-tubulin gene of the present invention; and identifying fungi belonging to genus *Geosmithia* based on the matching or difference.

The method of analyzing, and determining the nucleotide sequence is not particularly limited, and usual RNA or DNA sequencing means may be used.

Specific examples of the method include an electrophoresis method such as a Maxam-Gilbert method or a Sanger method, mass spectrometry, and a hybridization method. Examples of the Sanger method include a method of labeling a primer or terminator by a radiation labeling method, a fluorescent labeling method, or the like.

In the detection method of the present invention, the identification of fungi belonging to genus *Geosmithia* using a nucleic acid represented by a nucleotide sequence in variable region of the β-tubulin gene according to the present invention is preferably performed by hybridization using a nucleic acid probe targeted to the whole or partial region of the nucleotide sequence.

In the present invention, in order to identify and detect fungi belonging to genus *Geosmithia* using the nucleic acid represented by the nucleotide sequence in variable region of the β-tubulin gene of the present invention, an oligonucleotide for detection, which is hybridizable with the nucleic acid represented by the nucleotide sequence in variable region of the β-tubulin gene of the present invention and acts as a nucleic acid probe or a nucleic acid primer, may be used.

The oligonucleotide for detection of the present invention may be one which can be used for detecting fungi belonging to genus *Geosmithia*. That is, the oligonucleotide may be one which can be used as a nucleic acid primer or a nucleic acid probe for detecting fungi belonging to genus *Geosmithia*, or one which is hybridizable with the β-tubulin gene of fungi belonging to genus *Geosmithia* under stringent conditions. It should be note that the "stringent conditions" includes, for example, the method described in Molecular Cloning—A LABORATORY MANUAL THIRD EDITION [Joseph Sambrook, David W. Russell, Cold Spring Harbor Laboratory Press], and examples thereof include conditions where hybridization is performed by incubating a solution containing 6×SSC (composition of 1×SSC: 0.15M sodium chloride, 0.015M sodium citrate, pH7.0), 0.5% SDS, 5×Denhardt and 100 mg/mL herring sperm DNA together with a probe at 65° C. for 8 to 16 hours.

The oligonucleotide for detection of the present invention is preferably an oligonucleotide which is hybridizable with a region which is selected from the nucleotide sequence in variable region of the β-tubulin gene of the present invention and satisfies the following four conditions:

(1) including a region containing about 10 continuous nucleotides which are derived from the gene and have a nucleotide sequence specific to fungi belonging to genus *Geosmithia*;

(2) GC content of the oligonucleotide is about 30% to 80%;

(3) possibility to cause self-annealing in the oligonucleotide is low; and (4) Tm value of the oligonucleotide is about 55° C. or more. As used herein, the term "GC content" refers to the ratio (%) of the total number of guanine and cytosine bases to the total number of the bases in the oligonucleotide.

In the (1) above, the phrase "a region containing about 10 continuous nucleotides which are derived from the gene and have a nucleotide sequence specific to fungi belonging to genus *Geosmithia*" means a region where the nucleotide sequence is particularly poorly conserved among the different genera of fungi (that is, the region has particularly high specificity to fungi belonging to genus *Geosmithia*) and where a nucleotide sequence specific to fungi belonging to genus *Geosmithia* is present throughout about 10 continuous nucleotides, in variable region of the β-tubulin gene of the present invention.

Moreover, in the (3) above, the phrase "possibility to cause self-annealing in the oligonucleotide is low" means that the primer are expected not to bind in itself due to the nucleotide sequences of the primer.

The number of nucleotides in the oligonucleotide for detection of the present invention is not particularly limited, and is preferably 13 to 30, more preferably 18 to 23. The Tm value of the oligonucleotide in hybridization is preferably in a range of 55° C. to 65° C., more preferably 59° C. to 62° C. The GC content in the oligonucleotide is preferably 30% to 80%, more preferably 45% to 65%, most preferably about 55%.

The oligonucleotide for detection of the present invention is more preferably an oligonucleotide represented by the nucleotide sequence which is shown in SEQ ID NO: 4 or 5, or a complementary sequence thereof. Further, the oligonucleotide for detection of the present invention may be an oligonucleotide represented by a nucleotide sequence which shares 70% or more identity with the nucleotide sequence shown in SEQ ID NO: 4 or 5 or a complementary sequence thereof, and the identity is more preferably 80% or more, still more preferably 90% or more, particularly preferably 95% or more. Further, the oligonucleotide for detection which can be used in the present invention includes an oligonucleotide represented by a nucleotide sequence including a mutation(s) such as deletion, insertion or substitution of one or several, preferably one to five, more preferably one to four, still more preferably one to three, even more preferably one to two, particularly preferably one nucleotide in the nucleotide sequence shown in SEQ ID NO: 4 or 5 or a complementary sequence thereof, and an oligonucleotide represented by a modified nucleotide sequence. Moreover, an appropriate nucleotide sequence may be added to the nucleotide sequence shown in SEQ ID NO: 4 or 5 or a complementary sequence thereof.

The identity of nucleotide sequence is calculated, for example, by Lipman-Pearson method (Science, 227, 1435, (1985)). Specifically, it can be calculated by performing analysis using a homology analysis (Search homology) program of genetic information processing software Genetyx-Win (Software Development) while the unit size to compare (ktup) parameter is set to 2.

The oligonucleotide for detection of the present invention may be used as a nucleic acid primer and a nucleic acid probe. The nucleic acid probe can be prepared by labeling the above-mentioned oligonucleotide with a labeling substance. The labeling substance is not particularly limited and may be a usual labeling substance such as a radioactive substance, an enzyme, a fluorescent substance, a luminescent substance, an antigen, a hapten, an enzyme substrate, or an insoluble carrier. The oligonucleotide may be labeled at its terminal or at the sequence other than the terminals, or at the sugar, phosphate group, or base moiety. Examples of means for detecting the label include: autoradiography in the case of a nucleic acid probe labeled with a radioisotope; a fluorescent microscope in the case of a nucleic acid probe labeled with a fluorescent substance; and an analysis using a photosensitive film or a digital analysis using a CCD camera in the case of a nucleic acid probe labeled with a chemiluminescent substance.

Further, the oligonucleotide may be bound to a solid-phase carrier and used as a capture probe. In this case, the capture probe and labeled nucleic acid probe may be used in pairs in a sandwich assay, or a target nucleic acid may be labeled and captured.

In the detection method of the present invention, in order to identify and detect fungi belonging to genus *Geosmithia*, hybridization is performed using, as a nucleic acid probe, preferably the oligonucleotide defined in the following (c) or (d), more preferably the oligonucleotide represented by the nucleotide sequence shown in SEQ ID NO: 4 or 5.

(c) an oligonucleotide represented by the nucleotide sequence shown in SEQ ID NO: 4 or the complementary sequence thereof; or an oligonucleotide represented by a nucleotide sequence which shares 70% or more identity with the nucleotide sequence shown in SEQ ID NO: 4 or the complementary sequence thereof, and can be used as a nucleic acid probe;

(d) an oligonucleotide represented by the nucleotide sequence shown in SEQ ID NO: 5 or the complementary sequence thereof; or an oligonucleotide represented by a nucleotide sequence which shares 70% or more identity with the nucleotide sequence shown in SEQ ID NO: 5 or the complementary sequence thereof, and can be used as a nucleic acid probe.

In order to detect fungi belonging to genus *Geosmithia* in a test sample, an oligonucleotide represented by (c) and/or (d) is labeled to prepare a nucleic acid probe, and the resultant nucleic acid probe is hybridized with DNA or RNA, followed by detecting the label of the hybridized probe by an appropriate detection method. The nucleic acid probe is hybridized specifically with part of the variable region of the β-tubulin gene of fungi belonging to genus *Geosmithia*, and hence fungi belonging to genus *Geosmithia* in a test sample can be detected rapidly and easily. As a method of measuring the label of the nucleic acid probe hybridized with DNA or RNA, a usual method (such as a FISH method, a dot-blot method, a Southern-blot method, or a Northern-blot method) may be used.

Further, in the detection method of the present invention, in order to identify fungi belonging to genus *Geosmithia* using the nucleic acid represented by the nucleotide sequence in variable region of the β-tubulin gene of the present invention, a DNA fragment including the whole or a partial region of the nucleotide sequence is preferably amplified to confirm whether the amplified product is present or not. The method of amplifying the DNA fragment including the region is not particularly limited, and a usual method such as PCR (polymerase chain reaction) method, LCR (ligase chain reaction) method, SDA (strand displacement amplification) method, NASBA (nucleic acid sequence-based amplification) method, RCA (rolling-circle amplification) method, or the like may be used. However, in the present invention, the PCR method is preferably used from the viewpoint of rapidity and easiness.

In the present invention, a case where fungi belonging to genus *Geosmithia* are detected by using a PCR method is described.

In order to detect fungi belonging to genus *Geosmithia*, the oligonucleotide defined in the following (e) or (f) is preferably used as a nucleic acid primer, and the oligonucleotides represented by the nucleotide sequences shown in SEQ ID NOS: 4 and 5 are more preferably used.

(e) an oligonucleotide represented by the nucleotide sequence shown in SEQ ID NO: 4, or an oligonucleotide represented by a nucleotide sequence which shares 70% or more identity with the nucleotide sequence shown in SEQ ID NO: 4 and can be used as a nucleic acid primer;

(f) an oligonucleotide represented by the nucleotide sequence shown in SEQ ID NO: 5, or an oligonucleotide represented by a nucleotide sequence which shares 70% or more identity with the nucleotide sequence shown in SEQ ID NO: 5 and can be used as a nucleic acid primer.

Further, the nucleic acid primer pair for detecting fungi belonging to genus *Geosmithia* of the present invention is an oligonucleotide pair containing the oligonucleotides defined in the above (e) and (f).

The oligonucleotides of SEQ ID NO: 4 and SEQ ID NO: 5 are oligonucleotides having nucleotide sequences which are present in the β-tubulin gene region of fungi belonging to genus *Geosmithia* and have nucleotide sequences identical to a partial nucleotide sequences of the variable regions or complementary sequences thereof. These oligonucleotides are hybridizable specifically with parts of DNA of fungi belonging to genus *Geosmithia*.

The oligonucleotides defined in the above (e) and (f) correspond to the regions of the positions 62 to 79 and 223 to 243, respectively, in the nucleotide sequence shown in SEQ ID NO: 1; the regions of the positions 49 to 66 and 196 to 214, respectively, in the nucleotide sequence shown in SEQ ID NO: 2; and the regions of the positions 45 to 61 and 182 to 200, respectively, in the nucleotide sequence shown in SEQ ID NO: 3. Therefore, when the oligonucleotides are hybridized with the β-tubulin gene of fungi belonging to genus *Geosmithia*, fungi belonging to genus *Geosmithia* can be specifically detected.

Conditions of the PCR reaction in the present invention are not particularly limited as long as a DNA fragment of interest can be amplified to a detectable degree. A preferred example of the PCR reaction conditions is as follows. A cycle including: a thermal denaturation reaction for denaturation of double-stranded DNA into single strands at 95 to 98° C. for 10 to 60 seconds; an annealing reaction for hybridization of a primer pair with the single-stranded DNA at 55 to 59° C. for about 60 seconds; and an elongation reaction for a reaction of a DNA polymerase at about 72° C. for about 60 seconds; is repeated about 30 to 35 times.

In the present invention, confirmation of gene fragments amplified by the PCR method can be performed by a usual method. Examples of the method include, but not limited to, a method including performing electrophoresis for PCR reaction products and confirming the existence of a band corresponding to the size of the amplified gene, a method of measuring a time course of the amount of PCR reaction products, and a method of determining the nucleotide sequences of PCR reaction products. In the present invention, the method including performing electrophoresis after a gene amplification treatment and confirming the existence of a band corresponding to the size of the amplified gene is preferred. In the present invention, the detection of the gene fragments amplified by PCR method may be performed by conventional methods. Examples include, but are not limited to, a method of incorporating a nucleotide labeled with a radioactive substance or the like during the amplification reaction, a method using a primer labeled with a fluorescent substance or the like, and a method of incorporating a fluorescent substance capable of having an increased fluorescence intensity upon binding to DNA, such as ethidium bromide, between the two amplified DNA chains. In the present invention, the method of incorporating a fluorescent material capable of having an increased fluorescence intensity upon binding to DNA between the two amplified DNA chains is preferred.

In the case where a sample contains fungi belonging to genus *Geosmithia*, amplification of DNA fragments of about 150 to 180 bp specific to the fungi can be observed by performing a PCR reaction using the oligonucleotide pair of the present invention as a primer set followed by performing electrophoresis for the resultant PCR reaction products. The procedure can confirm whether the test sample contains fungi belonging to genus *Geosmithia*, regardless of whether it is a sexual or asexual generation.

In the present invention, the oligonucleotide for detection, nucleic acid primer, and nucleic acid probe to be used in the present invention may be chemically synthesized based on designed sequences or purchased from a manufacturer of reagents. Specifically, the primers may be synthesized using an oligonucleotide synthesizer or the like. Moreover, after synthesis, the oligonucleotides may be purified by an adsorption column, high-performance liquid chromatography, or electrophoresis before use. Furthermore, an oligonucleotide having a nucleotide sequence including substitution, deletion, insertion, or addition of one or several nucleotides may be synthesized by a known method.

The bonding pattern of the oligonucleotide for detection, nucleic acid primer and nucleic acid probe includes not only a phosphodiester bond present in a natural nucleic acid but also a phosphoroamidate bond and a phosphorothioate bond, or the like.

The test sample to be used in the present invention is not particularly limited and may be a food or drink itself, a raw material of the food or drink, isolated fungi, cultured fungi, or the like.

A method of preparing DNA from a test sample is not particularly limited as long as DNA can be obtained at a sufficient purity and in a sufficient amount for detecting fungi belonging to genus *Geosmithia*. While the test sample may be used without purification, the test sample may be subjected to a pre-treatment such as separation, extraction, concentration, or purification before use. For example, the test sample may be purified by phenol and chloroform extraction or using a commercially available extraction kit to increase the purity of the nucleic acid before use.

The oligonucleotide for detection, nucleic acid probe or nucleic acid primer according to the present invention may be preliminarily packaged together with various reagents necessary for detecting fungi belonging to genus *Geosmithia* so that a kit for use in the detection of fungi belonging to genus *Geosmithia* can be prepared.

The kit for detecting of the present invention includes, for example, the above-described oligonucleotide for detection of the present invention as a nucleic acid probe or the above-described oligonucleotide pair of the present invention as a nucleic acid primer pair. The kit can be preferably used in the case of detecting fungi belonging to genus *Geosmithia* by the hybridization method or the PCR method. The kit of the present invention may include not only the above-mentioned oligonucleotides for detection, nucleic acid probes or nucleic acid primers but also, depending on purpose, substances which are usually used for detecting fungi, such as a label-detecting substance, a buffer, a nucleic acid synthetase (such as a DNA polymerase, an RNA polymerase, or a reverse transcriptase), and an enzyme substrate (such as dNTP or rNTP).

According to the method of the present invention, a procedure from sample preparation to fungi detection can be performed within a time as short as about 5 to 12 hours.

EXAMPLES

Hereinafter, the present invention will be described more in detail with reference to Examples, but the present invention is not limited by the following Examples.

Example 1

Analysis of Nucleotide Sequence Specific to Fungi Belonging to Genus *Geosmithia*

Nucleotide sequences of β-tubulin genes derived from various fungi belonging to genus *Geosmithia* were determined by the following methods.

The fungi were cultured in the dark on a potato dextrose agar slant at 25° C. for 7 days, followed by extracting DNA using GenTorukun™ (manufactured by TAKARA BIO INC.). PCR amplification of a target site was performed using PuRe Taq™ Ready-To-Go PCR Beads (manufactured by GE Health Care UK LTD) and, as primers, Bt2a (5'-GGTAAC-CAAATCGGTGCTGCTTTC-3', SEQ ID NO: 6) and Bt2b (5'-ACCCTCAGTGTAGTGACCCTTGGC-3', SEQ ID NO: 7) (Glass and Donaldson, Appl Environ Microbiol 61:1323-1330, 1995). Amplification was performed under the conditions including a denaturation temperature of 95° C., an annealing temperature of 59° C., an elongation temperature of 72° C., and 35 cycles. PCR products were purified using Auto Seg™ G-50 (manufactured by Amersham Pharmacia Biotech). The PCR products were labeled with BigDye terminator Ver. 1.1 (manufactured by Applied Biosystems), and electrophoresis was performed using ABI PRISM 3130 Genetic Analyzer (manufactured by Applied Biosystems).

Nucleotide sequences from fluorescence signals in electrophoresis were determined using the software "ATGC Ver. 4" (manufactured by Genetyx).

Based on the nucleotide sequence information of the β-tubulin gene of a variety of fungi (*Geosmithia eburneus*, *Geosmithia byssochlamydoides*, *Geosmithia emersonii*, *Aspergillus niger* (Accession No.: AY585535), and *Cladosporium cladosporioides* (see Japanese patent application No. 2008-139999)), alignment analyses were performed using DNA analysis software (product name: DNAsis pro, manufactured by Hitachi Software Engineering Co., Ltd.), to thereby determine a specific region in the β-tubulin gene including nucleotide sequences specific to the fungi belonging to the genus *Geosmithia* (SEQ ID NOS: 1 to 3).

Example 2

Detection of Fungi Belonging to Genus *Geosmithia* by PCR Method (1) Preparation of Primers Among the determined nucleotide sequences specific to fungi belonging to genus *Geosmithia* (SEQ ID NOS: 1 to 3), from regions having particularly high specificity to fungi belonging to genus *Geosmithia* on the 3'-end side in the determined regions, partial regions which satisfy the following four conditions were searched:

1) about 10 continuous nucleotides sequence which is derived from the gene and specific to the genus is present;
2) GC content of the nucleotide is about 30% to 80%;
3) possibility to cause self-annealing in the oligonucleotide is low; and
4) Tm value of the oligonucleotide is about 55 to 65'C.

Based on the nucleotide sequences of the above partial regions, five primer pairs were designed to search the effectiveness of detection of the fungi belonging to genus *Geosmithia* by PCR reactions using DNAs extracted from the fungi as templates. Specifically, a study was performed on whether a DNA amplification reaction was observed on 150 to 180 bp in the reaction using DNA of genus *Geosmithia* as templates and whether no amplification product was observed in the reaction using genomic DNAs of other fungi as templates. As a result, among five primer pairs, one primer pair was found to be useful for the detection of genus *Geosmithia*. The primer pair confirmed to have the effectiveness is the primer pair consisting of oligonucleotide represented by SEQ ID NOS: 4 and 5. The primers were synthesized by Sigma-Aldrich Japan (desalted products, 0.02 μmol scale) and purchased.

(2) Preparation of Samples

The fungi shown in Tables 1 and 2 were used as fungi belonging to genus *Geosmithia*. For evaluation of the specificity of the primer consisting of the oligonucleotides represented by the nucleotide sequence shown in SEQ ID NOS: 4 and 5 to the β-tubulin gene of the fungi belonging to genus *Geosmithia*, other fungi belonging to genus *Geosmithia* and other fungi not belonging to genus *Geosmithia* shown in Tables 1 and 2 were also used. These fungi were stored in Medical Mycology Research Center, Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 1

| Sample No. | Scientific name | Strain No. |
| --- | --- | --- |
| 1 | *Geosmithia eburneus* | IFM53622(T7) |
| 2 | *Geosmithia eburneus* | IFM55257 |
| 3 | *Geosmithia byssochlamydoides* | IFM51198(T41) |
| 4 | *Geosmithia byssochlamydoides* | IFM48180 |
| 5 | *Geosmithia emersonii* | NBRC31232 |
| 6 | *Geosmithia emersonii* | NBRC31169 |
| 7 | *Talaromyces flavus* | IFM42243 |
| 8 | *Talaromyces flavus* | IFM52233 |
| 9 | *Talaromyces luteus* | IFM53242 |
| 10 | *Talaromyces luteus* | IFM53241 |
| 11 | *Talaromyces trachyspermus* | IFM42247 |
| 12 | *Talaromyces trachyspermus* | IFM52252 |
| 13 | *Talaromyces wortmannii* | IFM52255 |
| 14 | *Talaromyces wortmannii* | IFM52262 |
| 15 | *Byssochlamys fulva* | IFM48421 |
| 16 | *Byssochlamys fulva* | IFM51213 |
| 17 | *Byssochlamys nivea* | IFM51244 |
| 18 | *Byssochlamys nivea* | IFM51245 |
| 19 | *Hamigera avellanea* | IFM42323 |
| 20 | *Hamigera avellanea* | IFM52241 |

TABLE 2

| Sample No. | Scientific name | Strain No. |
| --- | --- | --- |
| 1 | *Geosmithia eburneus* | IFM53622(T7) |
| 2 | *Geosmithia emersonii* | NBRC31232 |
| 3 | *Paecilomyces variotii* | IFM40913 |
| 4 | *Paecilomyces variotii* | IFM40915 |
| 5 | *Neosartorya ficheri* | IFM46945 |
| 6 | *Neosartorya spinosa* | IFM46967 |
| 7 | *Neosartorya glabra* | IFM46949 |
| 8 | *Neosartorya hiratsukae* | IFM47036 |
| 9 | *Aspergillus fumigatus* | A125 |
| 10 | *Aspergillus niger* | An15 |
| 11 | *Aspergillus terreus* | A229 |
| 12 | *Aspergillus flavus* | As17 |
| 13 | *Emericella nidulans* | As18 |
| 14 | *Penicillium griseofulvum* | IFM54313 |
| 15 | *Penicillium citirinum* | IFM54314 |
| 16 | *Alternaria alternata* | IFM41348 |
| 17 | *Aureobasidium pullulans* | IFM41409 |
| 18 | *Chaetomium globosum* | IFM40869 |
| 19 | *Fusarium oxysporum* | IFM50002 |
| 20 | *Trichoderma viride* | IFM40938 |
| 21 | *Cladosporium cladosporioides* | IFM41450 |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/μL.

(4) PCR Reaction

One μL of the genomic DNA solution prepared above as a DNA template, 13 μL of Pre Mix Taq (trade name, manufactured by TAKARA BIO INC.) and 10 μL of sterile distilled water were mixed, and 0.5 μL of a primer consisting of an oligonucleotide represented by the nucleotide sequence shown in SEQ ID NO: 4 (Te1F primer: GTGGCCCT-CACGTTCGAG, 20 pmol/μL) and 0.5 μL of a primer consisting of an oligonucleotide represented by the nucleotide sequence shown in SEQ ID NO: 5 (Te1R primer: GCCAT-TGTAGCATGTGCCAA, 20 pmol/μL) were added thereto, to thereby prepare 25 μL of a PCR reaction solution.

The PCR reaction solution was subjected to a gene amplification reaction using an automatic gene amplification device, thermal cycler DICE (TAKARA BIO INC.). PCR reaction conditions were 35 cycles of (i) a thermal denaturation reaction at 95° C. for 1 minute, (ii) an annealing reaction at 55° C. for 1 minute, and (iii) an elongation reaction at 72° C. for 1 minute.

(5) Confirmation of Amplified Gene Fragment

Figure 2:
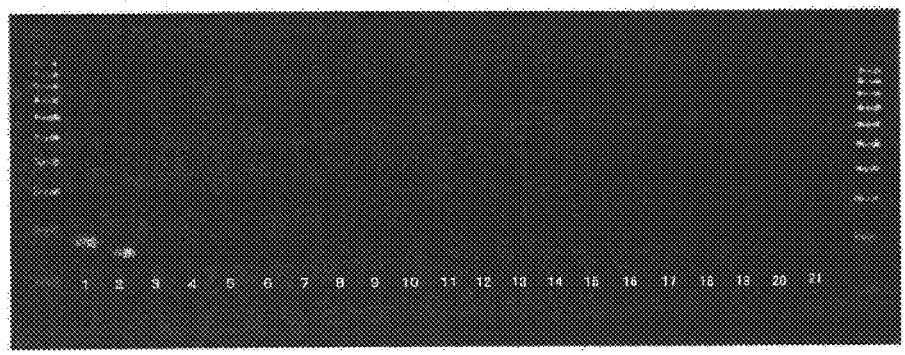
FIG. 2 An electrophoretogram of PCR products in Examples.

After the PCR reaction, 2.5 µL of a sample was collected from the PCR reaction solution and electrophoresed using a 2% agarose gel, and DNA was stained with SYBR Safe DNA gel stain in 1×TAE (Invitrogen), followed by fluorescence detection under ultraviolet light, to thereby confirm whether the amplified DNA fragment was present or not. FIG. 1 and FIG. 2 show an electrophoretogram in the agarose gel. Note that, FIG. 1 shows an electrophoretogram of samples of the fungi shown in Table 1, and FIG. 2 shows an electrophoretogram of samples of the fungi shown in Table 2. The numbers in the electrophoretograms represent samples which were subjected to reactions using DNAs extracted from samples of the corresponding sample numbers in the tables.

As a result, in the case of the samples containing the genomic DNA of fungi belonging to genus *Geosmithia* (lanes 1 to 6 in FIG. 1 and lanes 1 and 2 in FIG. 2), amplification of gene fragments of about 150 to 180 bp was confirmed. On the other hand, in the case of the samples containing no genomic DNA of fungi belonging to genus *Geosmithia*, amplification of gene fragments was not confirmed. The above-described results reveal that fungi belonging to genus *Geosmithia* can be specifically detected by using the oligonucleotides of the present invention.

INDUSTRIAL APPLICABILITY

According to the present invention, it is possible to provide a method capable of specifically, simply and quickly detecting fungi belonging to genus *Geosmithia*. Therefore, the present invention is useful in the fields of quality inspection of drinks and foods, quality inspection of pharmaceuticals and cosmetics, and environmental inspection in lines for manufacturing drinks, foods, pharmaceuticals, cosmetics, and the like.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2008-288639 filed in Japan on Nov. 11, 2008, which is entirely herein incorporated by reference.

What is claimed is:

1. A method of detecting whether a fungus belonging to genus *Geosmithia* is in a test sample, comprising
   (a) hybridizing, under stringent conditions, both
   (i) an oligonucleotide consisting of SEQ ID NO: 4, or an oligonucleotide consisting of a nucleotide sequence that has 90% or more identity with the nucleotide sequence of SEQ ID NO: 4 and
   (ii) an oligonucleotide consisting of SEQ ID NO: 5, or an oligonucleotide consisting of a nucleotide sequence that has 90% or more identity with the nucleotide sequence of SEQ ID NO: 5, to nucleic acid in the test sample or to nucleic acid obtained from the test sample; and
   (b) determining whether there is hybridization of both (i) and (ii) to the nucleic acid; wherein a fungus belonging to the genus *Geosmithia* is detected in the test sample when both (i) and (ii) hybridize to the nucleic acid.

2. The method according to claim 1, wherein the fungus belonging to genus *Geosmithia* is at least one species selected from the group consisting of *Geosmithia eburneus*, *Geosmithia emersonii* and *Geosmithia byssochlamydoides*.

3. The method of detecting a fungus belonging to genus *Geosmithia* according to claim 1, wherein (i) is the oligonucleotide consisting of SEQ ID NO: 4.

4. The method of detecting a fungus belonging to genus *Geosmithia* according to claim 1, wherein (ii) is the oligonucleotide consisting of SEQ ID NO: 5.

5. The method according to claim 1, wherein (i) is the oligonucleotide consisting of SEQ ID NO: 4 and (ii) is the oligonucleotide consisting of SEQ ID NO: 5.

6. The method of detecting a fungus belonging to genus *Geosmithia* according to claim 1, further comprising the steps of:
   performing gene amplification using (i) and (ii) as primers; and
   determining whether a gene amplification product is present or not as an indication of whether both (i) and (ii) hybridized to nucleic acid in the test sample.

7. The method according to claim 6, wherein the gene amplification reaction is performed by a polymerase chain reaction (PCR) method.

8. The method of claim 1, wherein said oligonucleotide (i) has 95% or more identity with the nucleotide sequence of SEQ ID NO: 4.

9. The method of claim 1, wherein said oligonucleotide (ii) has 95% or more identity with the nucleotide sequence of SEQ ID NO: 5.

10. The method of claim 1, wherein said oligonucleotide (i) has 95% or more identity with the nucleotide sequence of SEQ ID NO: 4 and said oligonucleotide (ii) has 95% or more identity with the nucleotide sequence of SEQ ID NO: 5.

* * * * *